United States Patent

Bruening et al.

Patent Number: 4,992,941
Date of Patent: Feb. 12, 1991

[54] COMPUTER TOMOGRAPHY APPARATUS WITH PERIODIC FOCUS DEFLECTION

[75] Inventors: Horst Bruening, Goessweinstein; Julius Brunner, Rueckersdorf; Günter Hahn, Neunkirchen Am Brand; Albrecht Baer, Buckenhof, all of Fed. Rep. of Germany

[73] Assignee: Siemens Aktiengesellschaft, Berlin and Munich, Fed. Rep. of Germany

[21] Appl. No.: 307,508

[22] Filed: Feb. 7, 1989

[30] Foreign Application Priority Data

Apr. 18, 1988 [DE] Fed. Rep. of Germany ....... 3812896
May 19, 1988 [DE] Fed. Rep. of Germany ....... 3817148

[51] Int. Cl.$^5$ .............................................. G06G 7/60
[52] U.S. Cl. ........................... 364/413.15; 364/413.16; 378/137
[58] Field of Search ...................... 364/413.16, 413.15; 378/137, 138

[56] References Cited

U.S. PATENT DOCUMENTS 4,002,917 1/1977 Mayo .............................. 250/455 T

FOREIGN PATENT DOCUMENTS 53-1322985 4/1977 Japan .
2138235 10/1984 United Kingdom .

Primary Examiner—Jerry Smith
Assistant Examiner—Steven Kibby
Attorney, Agent, or Firm—Hill, Van Santen, Steadman & Simpson

[57] ABSTRACT

A computer tomography apparatus has an x-ray source with a focus, with the focus being periodically deflected during data acquisition, specifically during mean value formation of the signals obtained by the radiation detector. The mean value formation is not undertaken simultaneously for all detector elements, but instead is undertaken chronologically offset from detector element to detector element. A memory in which the analog measured values available at the end of an interval would be stored is thus not needed.

4 Claims, 1 Drawing Sheet

COMPUTER TOMOGRAPHY APPARATUS WITH PERIODIC FOCUS DEFLECTION

BACKGROUND OF THE INVENTION

1. Field of the Invention

The present invention is directed to a computer tomography apparatus, and in particular to such an apparatus having a rotating frame surrounding a measuring region, with a radiation source and a row of detector elements being mounted on the frame.

2. Description of the Prior Art

Computer tomography devices are known in the art, such as that disclosed in German OS No. 2538517 corresponding to U.S. Pat. No. 4,002,917, which have a rotating frame on which a radiation source and a radiation detector are mounted. The radiation source generates a fan-shaped x-ray beam which penetrates an examination region in the interior of the frame, with radiation attenuated by a patient being incident on the radiation detector. The frame is rotatable around an axis extending through the measuring region, and disposed perpendicularly relative to the plane of the x-ray beam. The examination subject is thus transirradiated from different directions. A computer is provided which uses the data from the radiation detector to generate a cross-sectional image of the examination subject. This known device also has means for undertaking a periodic deflection of the focus of the x-ray source in the plane of the x-ray beam perpendicular to a center normal of the radiation detector In a computer tomography apparatus of this type, the measured values are described by two parameters. The first parameter, $\alpha$, identifies the angular position of the focus centroid relative to a fixed axis. The second parameter, $\beta$, is the angle between the central ray of the x-ray beam and a connecting line between the focus and the detector element under consideration.

If the focus in the rotating frame has a fixed position, i.e., is not deflected, there are as many different $\beta$ values as detector elements. If the focus is periodically deflected on either side of a point on the center normal of the detector, in a direction perpendicular to the center normal, measured values for a plurality of $\beta$ values can be acquired with a single, defined detector element. This means the total number of measured values is increased, and thus the image resolution can also be increased.

If S(t) is the function defining the periodic movement of the focus with respect to time t, then $S(t+T)=S(t)$ and $S(t+T/2)=-S(t)$ are valid, where T is the period of the focus deflection. The focus centroid in the interval $0 \leq t \leq T/2$ is different from the focus centroid in the interval $T/2 \leq t \leq T$.

Per detector element, a measured value in the first interval, and a further measured value in the second interval, can then be formed using integrators. Given a suitable selection of the amplitude of S(t), dependent on the shape on the function S, it can be achieved that the $\beta$ values for the second interval lie between the $\beta$ values of the first interval.

If all measured values in an interval are simultaneously formed, as in conventional devices, a memory must be provided in which the measured values available at the end of an interval are stored until derivation of a digital value proportional to the measured value. For example, a double integrator can be employed for each detector element for this purpose, the double integrator being switched at points in time n . T/2, with n being the number of measured data sets, and n = 1, 2 . .

SUMMARY OF THE INVENTION

It is an object of the present invention to provide a computer tomography apparatus with periodic deflection of the focus, wherein a more simple data acquisition system can be used.

The above object is achieved in accordance with the principles of the present invention in a computer tomography apparatus including means for periodically deflecting the focus of the x-ray source, wherein data is acquired so that the mean value formation ensues chronologically offset from detector element to detector element.

DESCRIPTION OF THE PREFERRED EMBODIMENTS

Figure 1:
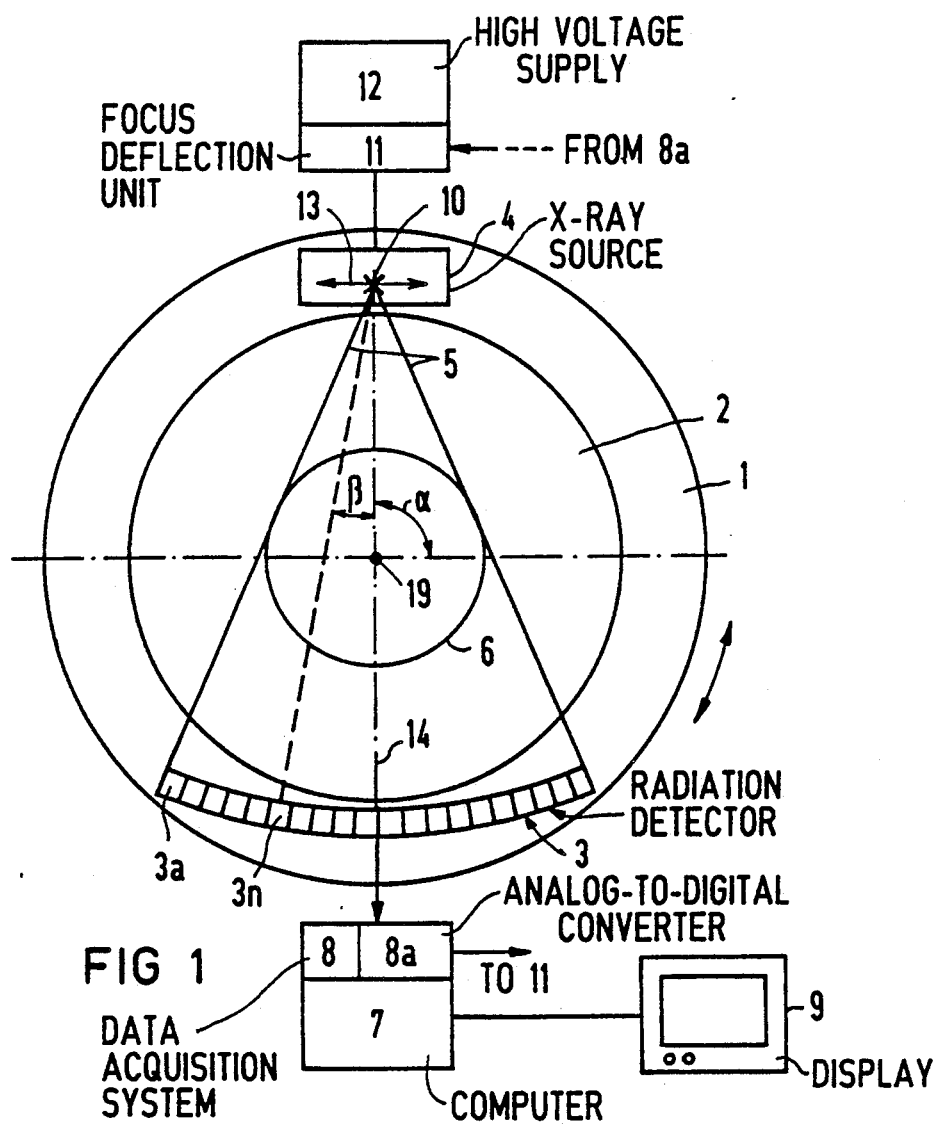
FIG. 1 is a schematic block diagram of a computer tomography apparatus constructed in accordance with the principles of the present invention.

A computer tomography apparatus constructed in accordance with the principles of the present invention is shown in FIG. 1. The apparatus includes a rotating frame 1 having a central opening defining a measuring or examination region 2. A radiation detector 3, consisting of a row of detector elements $3a \ldots 3n \ldots$, and an x-ray source 4 are mounted on the frame 1. The x-ray source 4 generates a fan-shaped x-ray beam 5 which is incident on the radiation detector 3, attenuated by a patient in the examination region 2. For transirradiation of a measuring field 6 in which an examination subject, for example a patient on a bed, is disposed from different directions, the frame 1 is rotated around an axis 19 extending through the measuring region 2, and thus through the measuring field 6, perpendicular to the fan plane of the x-ray beam 5. A computer 7 generates a cross-sectional image of the examination subject from the measured values from the radiation detector 3 acquired using a data acquisition system 8. The cross-sectional image is reproduced on a display 9. The data acquisition system 8 includes an analog-to-digital converter 8a for converting the analog output signals of the detector elements $3a \ldots$ into digital signals for further processing.

The focus 10 of the x-ray source 4 is periodically deflected in the direction of the double arrow 13, i.e., perpendicular to a center normal 14 of the radiation detector 3. The deflection of the focus 10 increases the number of measured values for each detector element $3a \ldots$. Deflection of the focus 10 is undertaken using a deflection unit 11 which is a part of a high voltage supply 12. The deflection unit 11 may have an input connected to the analog-to-digital converter 8a to control the deflection of the focus.

The angle $\alpha$ is shown in FIG. 1 for a focus centroid, and the angle $\beta$ is shown in FIG. 1 for the detector element 3n.

Figure 2:
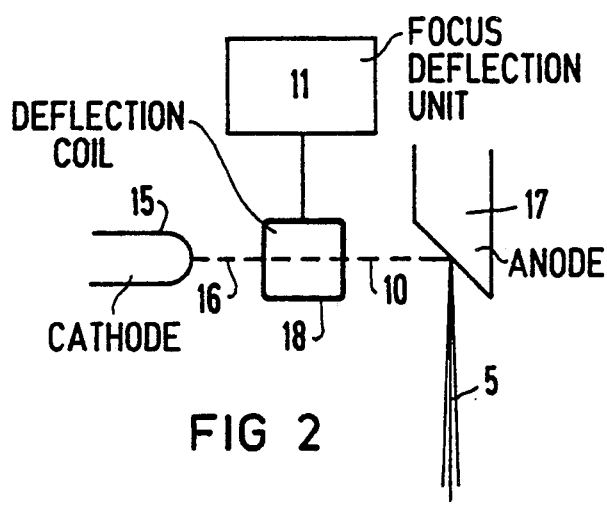
FIG. 2 is a block diagram of a portion of the tomography apparatus shown in 1 for explaining the operation of the device in greater detail.

The structure of the x-ray source 4 is shown in greater detail in FIG. 2, for accomplishing periodic deflection of the x-ray beam 5. A cathode 15 emits an electron beam 16 onto an anode 17, from which the x-ray beam 5 emanates such that the fan plane is disposed perpendicular to the plane of the drawing. Periodic focus deflection perpendicular to the plane of the drawing is undertaken using deflector coils 18, connected to the deflection unit 11.

As stated above, all of the measured values for the detector elements are not simultaneously formed, as is undertaken in conventional devices of this type.

In a first embodiment, two measured values are formed within the time of a focus deflection period per detector element $3a \ldots 3n \ldots$ It is assumed for simplification that only a single analog-to-digital converter is present in the data acquisition system 8, the analog signals from the individual measuring channels being supplied thereto in sequence. The $n^{th}$ measured value of the detector element, having the number v, is formed in the time domain according to the relationship:

$$n'T/2 + v'\Delta t \leq t \leq (n+1)'T/2 + v'\Delta t$$

ps with $v = 1, 2, \ldots N_D$, where $N_D$ is the number of detector elements. The symbol T is the duration of the period of the focus deflection, and t is time. The time interval $\Delta t$ between two successive analog-to-digital conversions must be sufficiently small such that $N_D \cdot \Delta t$ does not significantly exceed $T/4$.

The phases of the mean value formation for different v differ with respect to the focus movement S(t), however, measured values for $2 \cdot N_D$ different $\beta$ values are obtained. A set of measured values per detector element, wherein the focus centroid is deflected in one direction (for example, measured values having even-numbered n) and a second set of measured values, wherein the focus centroid is deflected in the other direction (measured values having odd-numbered n) are obtained. A suitable interpolation of these values permits projections to be produced, i.e., measured value sets for a fixed value $\alpha$ and for plurality of $\beta$ values lying equidistantly from each other. These projections contain more than $N_D$ values, for example, the projections may contain $2 \cdot N_D$ values. Fewer sampling errors than would be the case with projections containing only $N_D$ measured values result.

It is an important idea of the invention that the periodic deflection of the focus 10 be combined with a mean value formation which is chronologically offset ($\Delta t$) from detector element to detector element.

In a second embodiment, measured values are formed for each detector element with a frequency which is at least equal to four times the focus deflecting frequency. In the first embodiment, the frequency of the mean value formation is equal to twice the focus deflection frequency. The points in time $t_{vn}$, in which the analog measured values of a measuring channel v are supplied to one of the existing analog-to-digital converters, need not have a fixed phase relation to the focus deflection. The size of the mean focus deflection for the measuring interval, ending at a point in time $t_{vn}$, is identified by measuring the chronological position of $t_{vn}$ with respect to the periodic function S(t). Projections having more than $N_D$ values (for example $2N_D$ values) per projection can again be produced by a suitable combination of the data from a measuring channel associated with the same half period of the focus deflection and, as warranted, by an interpolation of the data generated in this manner in the $\beta$ direction.

Although modifications and changes may be suggested by those skilled in the art it is the intention of the inventors to embody within the patent warranted hereon all changes and modifications as reasonably and properly come within the scope of their contribution to the art.

We claim as our invention:

1. A computer tomography apparatus for examining a patient comprising:
    a frame having an opening for receiving a patient and rotatable around a central longitudinal axis extending through said opening;
    x-radiator means mounted on said frame for generating a fan-shaped x-ray beam in a plane perpendicular to said longitudinal axis for irradiating said patient in said opening, said x-radiator means having a focus from which said x-ray beam emanates;
    a radiation detector including a plurality of detector elements mounted on said frame and disposed to receive and detect x-radiation attenuated by said patient in said opening, each detector element generating a measured value corresponding to the x-radiation incident thereon, said radiation detector having a center normal;
    said frame with said x-radiator means and said radiation detector being rotatable around said patient in said opening to irradiate said patient from different directions;
    means for periodically deflecting said focus in the plane of said x-ray beam perpendicular to said center normal of said radiation detector;
    data processing means for acquiring said measured values of said detector elements and forming a mean value of the measured value of each detector element over a selected portion of the period of deflection of said focus, said selected portion being chronologically offset from detector element to detector element; and
    computer means for constructing an image of a cross-section of said patient from said mean values.

2. A computer tomography apparatus as claimed in claim 1 wherein said data processing means includes an analog-to-digital converter for successively converting analog signals from said detector elements into digital signals, and wherein said data processing means is a means for acquiring said measured values of said detector elements and forming a mean value in the offset time domains $$n \cdot T/2 + v \cdot \Delta t \leq t \leq (n+1) \cdot T/2 + v \cdot \Delta t$$

wherein $v = 1, 2, \ldots N_D$ and wherein said means for deflecting said focus is a means for deflecting said focus in one direction for measured values having even-numbered n and for deflecting said focus in an opposite direction for measured values having odd-numbered n; and wherein $N_D$ is the total number of detector elements, v is the number of a detector element within said radiation detector, n is the number of the measured value currently being formed into a mean value, T is the period of the focus deflection, t is time, and $\Delta t$ is the time interval between successive analog-to-digital conversions.

3. A computer tomography apparatus as claimed in claim 2 wherein said means for deflecting said focus is a means for deflecting said focus such that no focus deflection occurs during the time of said analog-to-digital conversions.

4. A computer tomography apparatus as claimed in claim 1 wherein said periodic deflection of said focus has a focus deflection frequency associated therewith, wherein said detector elements each generate measured values at a frequency at least four times the focus deflection frequency, wherein said data processing means includes an analog-to-digital converter for converting analog measured values from said detector elements into digital signals, wherein said data processing means includes means for supplying said analog values at points in time $t_{vn}$ to said analog-to-digital converter at an arbitrary phase relation to said focus deflection, wherein t is time, v is the number of a detector element, and n is the number of the measured value currently being processed, wherein said means for deflecting said focus is a means for deflecting said focus according to a periodic function $S(t)$ wherein said detector has $N_D$ detector elements, and wherein said data processing means is a means for combining said measured values of said detector elements so that more than $N_D$ mean values are formed during a period of said focus deflection.

* * * * *